US008821487B2

(12) United States Patent
Arts et al.

(10) Patent No.: US 8,821,487 B2
(45) Date of Patent: Sep. 2, 2014

(54) TEMPERATURE REGULATING PATIENT RETURN ELECTRODE AND RETURN ELECTRODE MONITORING SYSTEM

(75) Inventors: Gene H. Arts, Berthoud, CO (US); Paul Hermes, Guilford, CT (US)

(73) Assignee: Covidien AG (CH)

( * ) Notice: Subject to any disclaimer, the term of this patent is extended or adjusted under 35 U.S.C. 154(b) by 1386 days.

(21) Appl. No.: 11/395,683

(22) Filed: Mar. 31, 2006

(65) Prior Publication Data

US 2006/0224150 A1 Oct. 5, 2006

Related U.S. Application Data

(60) Provisional application No. 60/666,798, filed on Mar. 31, 2005.

(51) Int. Cl.
*A61B 18/16* (2006.01)
*A61B 18/12* (2006.01)
*A61N 1/04* (2006.01)
*A61B 17/00* (2006.01)
*A61B 18/00* (2006.01)

(52) U.S. Cl.
CPC ............. *A61B 18/16* (2013.01); *A61B 18/1233* (2013.01); *A61N 1/0408* (2013.01); *A61B 2017/00026* (2013.01); *A61B 2017/00084* (2013.01); *A61B 2018/00791* (2013.01); *A61N 1/0492* (2013.01)
USPC ............................................. 606/35; 606/32

(58) Field of Classification Search
CPC ............... A61B 18/1233; A61B 18/16; A61B 2018/00071; A61B 2018/00791; A61B 2018/167; A61B 2017/00026; A61B 2017/00084; A61N 1/0492

USPC ...................................................... 606/32–35
See application file for complete search history.

(56) References Cited

U.S. PATENT DOCUMENTS

| 2,536,271 A | 1/1951 | Fransen et al. |
| 3,380,445 A | 4/1968 | Frasier |

(Continued)

FOREIGN PATENT DOCUMENTS

| CA | 1 219642 | 3/1987 |
| DE | 3206947 | 9/1983 |

(Continued)

OTHER PUBLICATIONS

International Search Report PCT/US2004/004196 dated Oct. 4, 2007.

(Continued)

*Primary Examiner* — Michael Peffley
*Assistant Examiner* — Samantha Good (57) ABSTRACT

A temperature regulating patient return electrode and return electrode monitoring system for use in monopolar surgery, includes a positive temperature coefficient (PTC) material disposed on its surface. The PTC material responds to local increases in temperature by increasing local resistance. This quality decreases the probability of a patient burn as a result of monopolar surgery. The return electrode monitoring system includes a generator for generating current; an active electrode coupled to the generator for supplying the current to a patient; and a return electrode coupled to the generator with a surface for receiving the current from the patient and returning the current to the generator. A positive temperature coefficient (PTC) material is disposed on the return electrode for regulating the temperature over the surface of the return electrode.

23 Claims, 7 Drawing Sheets

(56) References Cited

U.S. PATENT DOCUMENTS

| | | | |
|---|---|---|---|
| 3,534,306 A | 10/1970 | Watrous et al. | |
| 3,543,760 A | 12/1970 | Bolduc | |
| 3,642,008 A | 2/1972 | Bolduc | |
| 3,683,923 A | 8/1972 | Anderson | |
| 3,812,861 A | 5/1974 | Peters | |
| 3,913,583 A | 10/1975 | Bross | |
| 3,923,063 A | 12/1975 | Andrews et al. | |
| 3,933,157 A | 1/1976 | Bjurwill et al. | |
| 3,987,796 A | 10/1976 | Gonser | |
| 4,067,342 A | 1/1978 | Burton | |
| 4,092,985 A | 6/1978 | Kaufman | |
| 4,094,320 A | 6/1978 | Newton et al. | |
| 4,102,341 A | 7/1978 | Ikuno et al. | |
| 4,114,622 A | 9/1978 | Gonser | |
| 4,117,846 A | 10/1978 | Williams | |
| 4,121,590 A | 10/1978 | Gonser | |
| 4,126,137 A | 11/1978 | Archibald | |
| 4,166,465 A | 9/1979 | Esty et al. | |
| 4,188,927 A | 2/1980 | Harris | |
| 4,200,104 A | 4/1980 | Harris | |
| 4,200,105 A | 4/1980 | Gonser | |
| 4,213,463 A | 7/1980 | Osenkarski | |
| 4,231,372 A | 11/1980 | Newton | |
| 4,237,887 A | 12/1980 | Gonser | |
| 4,253,721 A | 3/1981 | Kaufman | |
| 4,303,073 A | 12/1981 | Archibald | |
| 4,304,235 A | 12/1981 | Kaufman | |
| 4,331,149 A | 5/1982 | Gonser | |
| 4,343,308 A | 8/1982 | Gross | |
| 4,381,789 A | 5/1983 | Naser et al. | |
| 4,384,582 A | 5/1983 | Watt | |
| 4,387,714 A | 6/1983 | Geddes et al. | |
| 4,393,584 A | 7/1983 | Bare et al. | |
| 4,416,276 A | 11/1983 | Newton et al. | |
| 4,416,277 A | 11/1983 | Newton et al. | |
| 4,437,464 A | 3/1984 | Crow | |
| 4,494,541 A | 1/1985 | Archibald | |
| 4,643,193 A | 2/1987 | DeMarzo | |
| 4,657,015 A | 4/1987 | Irnich | |
| 4,658,819 A | 4/1987 | Harris et al. | |
| 4,662,369 A | 5/1987 | Ensslin | |
| 4,669,468 A | 6/1987 | Cartmell et al. | |
| 4,699,146 A | 10/1987 | Sieverding | |
| 4,722,761 A | 2/1988 | Cartmell et al. | |
| 4,725,713 A | 2/1988 | Lehrke | |
| 4,741,334 A | 5/1988 | Irnich | |
| 4,745,918 A | 5/1988 | Feucht | |
| 4,748,983 A | 6/1988 | Shigeta et al. | |
| 4,750,482 A | 6/1988 | Sieverding | |
| 4,754,757 A | 7/1988 | Feucht | |
| 4,768,514 A | 9/1988 | De Marzo | |
| 4,770,173 A | 9/1988 | Feucht et al. | |
| 4,788,977 A | 12/1988 | Farin et al. | |
| 4,799,480 A | 1/1989 | Abraham et al. | |
| 4,807,621 A | 2/1989 | Hagen et al. | |
| 4,844,063 A | 7/1989 | Clark | |
| 4,848,335 A | 7/1989 | Manes | |
| 4,862,889 A | 9/1989 | Feucht | |
| 4,873,974 A | 10/1989 | Hagen et al. | |
| 4,895,169 A | 1/1990 | Heath | |
| 4,942,313 A | 7/1990 | Kinzel | |
| 4,947,846 A | 8/1990 | Kitagawa et al. | |
| 4,955,381 A | 9/1990 | Way et al. | |
| 4,961,047 A | 10/1990 | Carder | |
| 4,969,885 A | 11/1990 | Farin | |
| 5,000,753 A | 3/1991 | Hagen et al. | |
| 5,004,425 A | 4/1991 | Hee | |
| 5,010,896 A | 4/1991 | Westbrook | |
| 5,038,796 A | 8/1991 | Axelgaard et al. | |
| 5,042,981 A | 8/1991 | Gross | |
| 5,061,914 A | 10/1991 | Busch et al. | |
| 5,087,257 A | 2/1992 | Farin | |
| 5,114,424 A | 5/1992 | Hagen et al. | |
| 5,152,762 A | 10/1992 | McElhenney | |
| 5,160,334 A | 11/1992 | Billings et al. | |
| 5,196,008 A | 3/1993 | Kuenecke | |
| 5,246,439 A | 9/1993 | Hebborn et al. | |
| 5,271,417 A | 12/1993 | Swanson et al. | |
| 5,276,079 A | 1/1994 | Duan et al. | |
| 5,286,255 A | 2/1994 | Weber | |
| 5,312,401 A | 5/1994 | Newton et al. | |
| 5,336,255 A | 8/1994 | Kanare et al. | |
| 5,352,315 A | 10/1994 | Carrier et al. | |
| 5,362,420 A | 11/1994 | Itoh et al. | |
| 5,370,645 A | 12/1994 | Klicek et al. | |
| 5,385,679 A | 1/1995 | Uy et al. | |
| 5,388,490 A | 2/1995 | Buck | |
| 5,389,376 A | 2/1995 | Duan et al. | |
| 5,390,382 A | 2/1995 | Hannant et al. | |
| 5,409,966 A | 4/1995 | Duan et al. | |
| 5,447,513 A | 9/1995 | Davison et al. | |
| 5,449,365 A | 9/1995 | Green et al. | |
| 5,452,725 A | 9/1995 | Martenson | |
| 5,480,399 A | 1/1996 | Hebborn | |
| 5,496,312 A | 3/1996 | Klicek | |
| 5,496,363 A | 3/1996 | Burgio et al. | |
| 5,520,180 A | 5/1996 | Uy et al. | |
| 5,536,446 A | 7/1996 | Uy et al. | |
| 5,540,684 A | 7/1996 | Hassler, Jr. | |
| 5,599,347 A | 2/1997 | Hart et al. | |
| 5,601,618 A | 2/1997 | James | |
| 5,611,709 A | 3/1997 | McAnulty | |
| 5,632,280 A | 5/1997 | Leyde et al. | |
| 5,643,319 A | 7/1997 | Green et al. | |
| 5,660,892 A | 8/1997 | Robbins et al. | |
| 5,670,557 A | 9/1997 | Dietz et al. | |
| 5,674,561 A | 10/1997 | Dietz et al. | |
| 5,678,545 A | 10/1997 | Stratbucker | |
| 5,688,269 A | 11/1997 | Newton et al. | |
| 5,695,494 A | 12/1997 | Becker | |
| 5,707,369 A | 1/1998 | Vaitekunas et al. | |
| 5,718,719 A * | 2/1998 | Clare et al. | 607/5 |
| 5,720,744 A | 2/1998 | Eggleston et al. | |
| 5,766,165 A | 6/1998 | Gentelia et al. | |
| 5,779,632 A | 7/1998 | Dietz et al. | |
| 5,797,902 A | 8/1998 | Netherly | |
| 5,800,426 A | 9/1998 | Taki et al. | |
| 5,817,091 A | 10/1998 | Nardella et al. | |
| 5,830,212 A | 11/1998 | Cartmell et al. | |
| 5,836,942 A | 11/1998 | Netherly et al. | |
| 5,846,558 A | 12/1998 | Nielsen et al. | |
| 5,853,750 A | 12/1998 | Dietz et al. | |
| 5,868,742 A | 2/1999 | Manes et al. | |
| 5,924,983 A | 7/1999 | Takaki et al. | |
| 5,947,961 A | 9/1999 | Netherly | |
| 5,952,398 A | 9/1999 | Dietz et al. | |
| 5,971,981 A | 10/1999 | Hill et al. | |
| 5,976,128 A | 11/1999 | Schilling et al. | |
| 5,985,990 A | 11/1999 | Kantner et al. | |
| 5,999,061 A | 12/1999 | Pope et al. | |
| 6,007,532 A | 12/1999 | Netherly | |
| 6,010,054 A | 1/2000 | Johnson et al. | |
| 6,030,381 A | 2/2000 | Jones et al. | |
| 6,032,063 A | 2/2000 | Hoar et al. | |
| 6,039,732 A | 3/2000 | Ichikawa et al. | |
| 6,053,910 A | 4/2000 | Fleenor | |
| RE36,720 E | 5/2000 | Green et al. | |
| 6,059,778 A | 5/2000 | Sherman | |
| 6,063,075 A | 5/2000 | Mihori | |
| 6,083,221 A | 7/2000 | Fleenor et al. | |
| 6,086,249 A | 7/2000 | Urich | |
| 6,121,508 A | 9/2000 | Bischof et al. | |
| 6,135,953 A | 10/2000 | Carim | |
| 6,171,304 B1 | 1/2001 | Netherly et al. | |
| 6,200,314 B1 | 3/2001 | Sherman | |
| 6,203,541 B1 | 3/2001 | Keppel | |
| 6,214,000 B1 | 4/2001 | Fleenor et al. | |
| 6,232,366 B1 | 5/2001 | Wang et al. | |
| 6,240,323 B1 | 5/2001 | Calenzo, Sr. et al. | |
| 6,258,085 B1 | 7/2001 | Eggleston | |
| 6,275,786 B1 | 8/2001 | Daners | |
| 6,301,500 B1 | 10/2001 | van Herk et al. | |
| 6,310,611 B1 | 10/2001 | Caldwell | |
| 6,347,246 B1 | 2/2002 | Perrault et al. | |

(56) References Cited

U.S. PATENT DOCUMENTS

| | | |
|---|---|---|
| 6,350,264 B1 | 2/2002 | Hooven |
| 6,357,089 B1 | 3/2002 | Koguchi et al. |
| 6,358,245 B1 | 3/2002 | Edwards et al. |
| 6,379,161 B1 | 4/2002 | Ma |
| 6,409,722 B1 | 6/2002 | Hoey et al. |
| 6,413,255 B1 | 7/2002 | Stern |
| 6,415,170 B1 | 7/2002 | Loutis et al. |
| 6,454,764 B1 | 9/2002 | Fleenor et al. |
| 6,488,678 B2 | 12/2002 | Sherman |
| 6,537,272 B2 | 3/2003 | Christopherson et al. |
| 6,544,258 B2 | 4/2003 | Fleenor et al. |
| 6,546,270 B1 | 4/2003 | Goldin et al. |
| 6,565,559 B2 * | 5/2003 | Eggleston ........................ 606/35 |
| 6,569,160 B1 | 5/2003 | Goldin et al. |
| 6,582,424 B2 | 6/2003 | Fleenor et al. |
| 6,666,859 B1 | 12/2003 | Fleenor et al. |
| 6,669,073 B2 | 12/2003 | Milliman et al. |
| 6,736,810 B2 | 5/2004 | Hoey et al. |
| 6,796,828 B2 | 9/2004 | Ehr et al. |
| 6,799,063 B2 | 9/2004 | Carson |
| 6,830,569 B2 | 12/2004 | Thompson et al. |
| 6,849,073 B2 | 2/2005 | Hoey et al. |
| 6,860,881 B2 | 3/2005 | Sturm |
| 6,875,210 B2 | 4/2005 | Refior et al. |
| 6,892,086 B2 | 5/2005 | Russell |
| 6,905,497 B2 | 6/2005 | Truckai et al. |
| 6,939,344 B2 | 9/2005 | Kreindel |
| 6,948,503 B2 | 9/2005 | Refior et al. |
| 6,953,139 B2 | 10/2005 | Milliman et al. |
| 6,959,852 B2 | 11/2005 | Shelton, IV et al. |
| 6,997,735 B2 | 2/2006 | Ehr et al. |
| 7,025,765 B2 | 4/2006 | Balbierz et al. |
| 7,128,253 B2 | 10/2006 | Mastri et al. |
| 7,143,926 B2 | 12/2006 | Shelton, IV et al. |
| 7,160,293 B2 | 1/2007 | Sturm et al. |
| 7,166,102 B2 | 1/2007 | Fleenor et al. |
| 7,169,144 B2 | 1/2007 | Hoey et al. |
| 7,169,145 B2 | 1/2007 | Isaacson et al. |
| 7,182,604 B2 | 2/2007 | Ehr et al. |
| 7,220,260 B2 | 5/2007 | Fleming et al. |
| 7,229,307 B2 | 6/2007 | Ehr et al. |
| 7,258,262 B2 | 8/2007 | Mastri et al. |
| 7,267,675 B2 | 9/2007 | Stern et al. |
| 7,278,562 B2 | 10/2007 | Mastri et al. |
| 7,303,107 B2 | 12/2007 | Milliman et al. |
| 7,308,998 B2 | 12/2007 | Mastri et al. |
| 7,311,560 B2 | 12/2007 | Ehr et al. |
| 7,357,287 B2 | 4/2008 | Shelton, IV et al. |
| 7,380,695 B2 | 6/2008 | Doll et al. |
| 7,422,589 B2 | 9/2008 | Newton et al. |
| 7,473,145 B2 | 1/2009 | Ehr et al. |
| 2003/0139741 A1 | 7/2003 | Goble et al. |
| 2003/0199870 A1 * | 10/2003 | Truckai et al. .................. 606/51 |
| 2004/0059323 A1 | 3/2004 | Sturm et al. |
| 2004/0150504 A1 | 8/2004 | Nicholson |
| 2005/0021022 A1 | 1/2005 | Sturm et al. |
| 2005/0079752 A1 | 4/2005 | Ehr et al. |
| 2005/0085806 A1 | 4/2005 | Auge, II et al. |
| 2005/0101947 A1 | 5/2005 | Jarrard et al. |
| 2005/0251130 A1 | 11/2005 | Boveja et al. |
| 2006/0030195 A1 | 2/2006 | Ehr et al. |
| 2006/0041251 A1 | 2/2006 | Odell et al. |
| 2006/0041252 A1 | 2/2006 | Odell et al. |
| 2006/0041253 A1 | 2/2006 | Newton et al. |
| 2006/0074411 A1 | 4/2006 | Carmel et al. |
| 2006/0079872 A1 | 4/2006 | Eggleston |
| 2006/0173250 A1 | 8/2006 | Nessler |
| 2006/0217742 A1 | 9/2006 | Messerly et al. |
| 2006/0224150 A1 | 10/2006 | Arts et al. |
| 2007/0049914 A1 | 3/2007 | Eggleston |
| 2007/0049916 A1 | 3/2007 | Isaacson et al. |
| 2007/0049919 A1 | 3/2007 | Lee. Jr. et al. |
| 2007/0073284 A1 | 3/2007 | Sturm |
| 2007/0074719 A1 | 4/2007 | Danek et al. |
| 2007/0161979 A1 | 7/2007 | McPherson |
| 2007/0167942 A1 | 7/2007 | Rick |
| 2007/0203481 A1 | 8/2007 | Gregg et al. |
| 2007/0244478 A1 | 10/2007 | Bahney |
| 2008/0009846 A1 | 1/2008 | Ward |
| 2008/0033276 A1 | 2/2008 | Ehr et al. |
| 2008/0083806 A1 | 4/2008 | Scirica |
| 2008/0083813 A1 | 4/2008 | Zemlok et al. |
| 2008/0249520 A1 | 10/2008 | Dunning et al. |
| 2008/0249524 A1 | 10/2008 | Dunning |
| 2008/0281309 A1 | 11/2008 | Dunning et al. |
| 2008/0281310 A1 | 11/2008 | Dunning et al. |
| 2008/0281311 A1 | 11/2008 | Dunning et al. |
| 2009/0036884 A1 | 2/2009 | Gregg et al. |
| 2009/0036885 A1 | 2/2009 | Gregg |

FOREIGN PATENT DOCUMENTS

| | | |
|---|---|---|
| DE | 3544443 | 6/1987 |
| DE | 42 38 263 A1 | 5/1993 |
| DE | 4231236 | 3/1994 |
| DE | 197 17 411 A1 | 11/1998 |
| DE | 198 01 173 | 7/1999 |
| DE | 103 28 514 | 6/2003 |
| DE | 102004010940 | 9/2005 |
| EP | 0262888 | 4/1988 |
| EP | 390937 | 10/1990 |
| EP | 836868 | 4/1998 |
| EP | 0 930 048 | 7/1999 |
| EP | 1 051 949 A1 | 11/2000 |
| EP | 1076350 | 2/2001 |
| EP | 1 468 653 | 10/2004 |
| EP | 1 645 236 | 4/2006 |
| EP | 1707151 | 10/2006 |
| EP | 1 808 144 | 7/2007 |
| EP | 1902684 | 3/2008 |
| FR | 2276027 | 6/1974 |
| FR | 2516782 | 5/1983 |
| GB | 2 054 382 | 2/1981 |
| GB | 2374532 | 10/2002 |
| WO | WO 96/19152 | 6/1996 |
| WO | WO 97/37719 | 10/1997 |
| WO | WO 98/18395 | 5/1998 |
| WO | WO 98/53751 | 12/1998 |
| WO | WO 99/09899 * | 3/1999 |
| WO | WO 99/11187 | 3/1999 |
| WO | WO 00/06246 | 2/2000 |
| WO | WO 00/32122 | 6/2000 |
| WO | WO 00/53113 | 9/2000 |
| WO | WO 00/65993 | 11/2000 |
| WO | WO 01/87175 | 11/2001 |
| WO | WO 02/058579 | 8/2002 |
| WO | WO 02/060526 | 8/2002 |
| WO | WO 02/099442 | 12/2002 |
| WO | WO 03/094766 | 11/2003 |
| WO | WO 2004/028385 | 4/2004 |
| WO | WO 2004/074854 | 9/2004 |
| WO | WO 2005/048809 | 6/2005 |
| WO | WO 2005/087124 | 9/2005 |
| WO | WO 2005/099606 | 10/2005 |
| WO | WO 2005/110263 | 11/2005 |
| WO | WO 2005/115262 | 12/2005 |
| WO | WO 2008/009385 | 1/2008 |

OTHER PUBLICATIONS

International Search Report EP06006961.4 dated Oct. 5, 2007.
International Search Report EP07000885.9 dated May 2, 2007.
International Search Report EP07007783.9 dated Aug. 6, 2007.
International Search Report EP06018206.0 dated Oct. 13, 2006.
International Search Report EP 05021944.3 dated Jan. 25, 2006.
International Search Report EP 05002027.0 dated May 12, 2005.
International Search Report from EP 06006961 dated Aug. 3, 2006.
Boyles, Walt; "Instrumentation Reference Book", 2002; Butterworth-Heinemann ; 262-264.
International Search Report EP06023756.7 dated Feb. 21, 2008.
International Search Report EP07018375.1 dated Jan. 8, 2008.
International Search Report EP07019173.9 dated Feb. 12, 2008.
International Search Report EP07019178.8 dated Feb. 12, 2008.

(56) References Cited

OTHER PUBLICATIONS

International Search Report EP07253835.8 dated Feb. 20, 2007.
International Search Report EP08006731.7 dated Jul. 29, 2008.
International Search Report EP08006734.1 dated Aug. 18, 2008.
International Search Report EP07000567.3 dated Dec. 3, 2008.
International Search Report EP08006731 dated Jul. 14, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
Examiner's First Report issued in corresponding Australian Appl. No. 2006201356 dated Nov. 16, 2010.
Australian Examiner's Report dated Dec. 7, 2011 in related Australian Application No. 2006201356.

\* cited by examiner

TEMPERATURE REGULATING PATIENT RETURN ELECTRODE AND RETURN ELECTRODE MONITORING SYSTEM

CROSS REFERENCE TO RELATED PATENT APPLICATIONS

The instant patent application claims priority to U.S. Provisional Patent Application Ser. No. 60/666,798 to Arts, et al., filed on Mar. 31, 2005, which is herein incorporated by reference in its entirety.

BACKGROUND

1. Technical Field

The present disclosure is directed to electrosurgical apparatus and systems, and, in particular, to a temperature regulating patient return electrode and a return electrode monitoring system for use in electrosurgery.

2. Description of the Related Art

During electrosurgery, a source or active electrode delivers energy, such as radio frequency energy, from an electrosurgical generator to the patient and a return electrode carries the current back to the electrosurgical generator. In monopolar electrosurgery, the source electrode is typically a hand-held instrument placed by the surgeon at the surgical site and the high current density flow at this electrode creates the desired surgical effect of cutting or coagulating tissue. The patient return electrode is placed at a remote site from the source electrode and is typically in the form of a pad adhesively adhered to the patient.

The return electrode has a large patient contact surface area to minimize heating at that site since the smaller the surface area, the greater the current density and the greater the intensity of the heat. That is, the area of the return electrode that is adhered to the patient is important because it is the current density of the electrical signal that heats the tissue. A larger surface contact area is desirable to reduce heat intensity. The size of return electrodes are based on assumptions of the maximum current seen in surgery and the duty cycle (e.g., the percentage of time the generator is on) during the procedure. The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and, in turn, increasing the heat applied to the tissue. This risked burning the patient in the area under the adhered portion of the return electrode if the tissue was heated beyond the point where circulation of blood could cool the skin.

To address this problem, split return electrodes and hardware circuits, generically called Return Electrode Contact Quality Monitors (RECQMs), were developed. These split electrodes consist of two separate conductive foils arranged as two halves of a single return electrode. The hardware circuit uses an AC signal between the two electrode halves to measure the impedance therebetween. This impedance measurement is indicative of how well the return electrode is adhered to the patient since the impedance between the two halves is directly related to the area of patient contact. That is, if the electrode begins to peel from the patient, the impedance increases since the contact area of the electrode decreases. Current RECQMs are designed to sense this change in impedance so that when the percentage increase in impedance exceeds a predetermined value or the measured impedance exceeds a threshold level, the electrosurgical generator is shut down to reduce the chances of burning the patient.

Although monitoring circuits are effective, they do not take into account the amount of time the current is being delivered or the heat generated at the return electrode. As new surgical procedures continue to be developed that utilize higher current and higher duty cycles, increased heating of tissue under the return electrode will occur.

U.S. Pat. No. 4,657,015 discloses a control device for cutting off high frequency current during electrosurgery if the heat buildup in the body tissue exceeds a predetermined value. In the '015 patent, a control electrode is affixed to the body spaced from the active electrode and separate from the neutral (i.e., return) electrode. The control electrode is designed to pick up the voltage existing on the body. The voltage signal is squared, integrated over time and compared to a reference voltage. The high frequency generator is turned off if the voltage value exceeds the reference voltage. The '015 patent does not effectively measure heating under the return electrode since the measurements are calculated by a separate control electrode. The '015 patent even states that the effective surface area of the neutral electrode is not a factor in the heat calculations.

U.S. Pat. No. 4,741,334 discloses a control circuit intended to reduce burning of tissue. As in the '015 patent, a separate control electrode is provided to determine the body voltage. The control electrode is spaced from the neutral electrode (i.e., the return electrode) and functions to detect a high frequency body surface voltage. The body surface voltage is converted into DC voltage by a converter and inputted to a comparator for comparison to a reference voltage. The generator is turned off if the body voltage exceeds the reference voltage. The '015 patent also discloses a monitor circuit for testing whether the neutral electrode is in good contact with the body surface of the patient. The comparator compares the body surface voltage detected by the control electrode with a reference voltage derived from the operational voltage of the surgical device. An audible signal is produced when these voltage values reach a predetermined ratio. Similar to the '015 patent, the '334 patent requires an additional electrode, measures voltage instead of current to determine overheating, and does not factor in the amount of time the high frequency energy is being applied.

SUMMARY

The present disclosure provides a temperature regulating patient return electrode and return electrode temperature monitoring system. The return electrode, for use in monopolar surgery, includes a positive temperature coefficient (PTC) material on, or coating the return electrode. The PTC material responds to increases in localized temperature by increasing local resistance which in turn reduces current flow and lowers the temperature. This quality helps limit the probability of a patient suffering from a burn as a result of monopolar surgery.

In several contemplated embodiments, the return electrode is a pad comprised of different layers of material. At least one of the layers is a PTC material, such as a polymer/carbon based material, a cermet based material, a polymer material, a ceramic material, a dielectric material, or any combinations thereof. Another material that can be used for the PTC material is described in U.S. Pat. No. 6,132,426, the contents of which is herein incorporated by reference in its entirety, and is known as "PolySwitch RTM" made by the Raychem Corporation of California. In one embodiment, a top layer of the return electrode comprises an adhesive material for coming into contact with and adhering to the patient. This layer of adhesive helps to ensure an optimal patient contacting surface area, i.e., the portion of the return electrode that is in contact with the patient. The adhesive can be made of, but is not limited to, a polyhesive adhesive, a Z-axis adhesive, or a water-insoluble, hydrophilic, pressure-sensitive adhesive, as described in U.S. Pat. Nos. 4,699,146 and 4,750,482, the contents of which are herein incorporated by reference in its entirety.

In one aspect of the present disclosure, the return electrode monitoring system includes a generator for supplying current, a surgical instrument, a cable for transferring current from the generator to the surgical instrument, a return electrode having a PTC material for receiving the current through a patient, and a wire for returning the current from the return electrode back to the generator.

A return electrode monitor (REM) may be incorporated into the system to provide temperature monitoring, current monitoring, impedance monitoring, energy monitoring, power monitoring and/or contact quality monitoring for the return electrode. The REM can be part of or attached to the generator with wires connecting the REM to the return electrode. Further, the REM can disable the generator if the temperature of the return electrode reaches or exceeds a predetermined value.

In one embodiment, the return electrode is split into at least two parts. In this embodiment, the return electrodes enable various measurements (e.g., temperature, current, contact quality, impedance, etc.) to be taken between the return electrodes. In a related embodiment, the parts of the return electrode can be interlocking, thus providing an increased surface area between the return electrodes.

In another embodiment, a plurality of wires is disposed on the return electrode, such that the wires form a grid or matrix pattern. This embodiment enables various measurements (e.g., temperature, current, voltage, etc.) to be calculated at various places on the return electrode by determining the resistance between any two wires. An individual wire may be coupled to each pad of the plurality of pads for determining a resistance or impedance between any two individual wires.

Another embodiment of the present disclosure includes an electrosurgical system for eliminating patient burns during monopolar surgery. The system has a generator for generating current, an active electrode coupled to the generator configured to supply the current to a patient; and a return electrode coupled to the generator having a defined surface. The surface is configured to receive the current from the patient and return the current to the generator. A positive temperature coefficient (PTC) material is disposed on the return electrode which regulates the temperature over the surface of the return electrode. The PTC material may be configured to regulate a current density at the return electrode. The PTC layer may be a substantially continuous coating of parallel resistors and alternatively, the PTC layer may have at least four parallel resistors.

The electrosurgical system may include a temperature regulation device disposed in the generator for regulating temperature at the return electrode. Alternatively, the electrosurgical system may include a temperature monitoring device disposed in the generator for monitoring temperature at the return electrode and/or a generator disabling device disposed in the generator for disabling the generator when the temperature of the return electrode reaches a predetermined value. A return electrode monitor may also be included for monitoring temperature and/or a contact quality of the return electrode.

An individual wire may be coupled to each pad of a plurality of electrode pads and the system is configured to determine a parameter between any two individual wires. The parameter may be selected from the group consisting of power, resistance, impedance, and any combination thereof.

A method for eliminating patient burns while performing monopolar surgery is also disclosed. The method includes the steps of: placing a return electrode coated with a positive temperature coefficient (PTC) material in contact with a patient; generating electrosurgical energy; and supplying the electrosurgical energy to the patient via an active electrode. The PTC material coating the return electrode regulates the temperature over the return electrode by responding to increases in localized temperature with a local increase in resistance. This spreads the temperature over the surface of the electrode.

Another example of the present disclosure includes an electrosurgical generator having a processor. A supply electrode is connected to the generator and is configured to deliver radiofrequency energy to a patient. A return electrode is connected to a return of the electrosurgical generator. The return electrode has a plurality of return electrode portions and an impedance sensor measures impedance values between the return electrode portions. The sensor outputs the impedance values to the processor to determine a contact reading. The processor compares the contact reading to a stored threshold reading to determine a degree of adherence of the return electrode on the patient. The processor may be configured to adjust or interrupt radiofrequency energy to the patient when the contact reading in indicative of poor adherence of the return electrode on the patient.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the presently disclosed temperature regulating patient return electrode and return electrode monitoring system will be described herein below with reference to the accompanying drawing figures wherein like reference numerals identify similar or identical elements. In the following description, well-known functions or constructions are not described in detail to avoid obscuring the disclosure in unnecessary detail.

Figure 1:
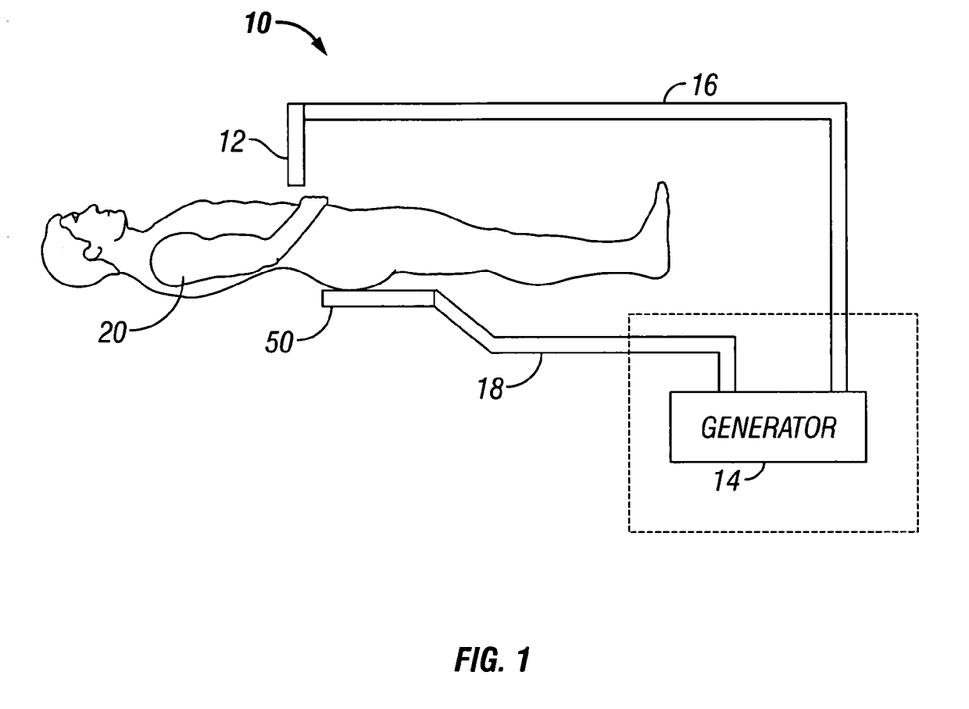
FIG. 1 is a schematic illustration of a monopolar electrosurgical system.

Referring initially to FIG. 1, a schematic illustration of a monopolar electrosurgical system 10 is shown. A surgical instrument (e.g., an active electrode) for treating tissue at the surgical site is designated by reference number 12. Electrosurgical energy is supplied to instrument 12 by generator 14 via cable 16 to cut, coagulate, etc. tissue. A return electrode, designated by reference numeral 50, is shown placed under a patient 20 to return the energy from the patient 20 back to the generator 14 via a wire 18.

Figure 2:
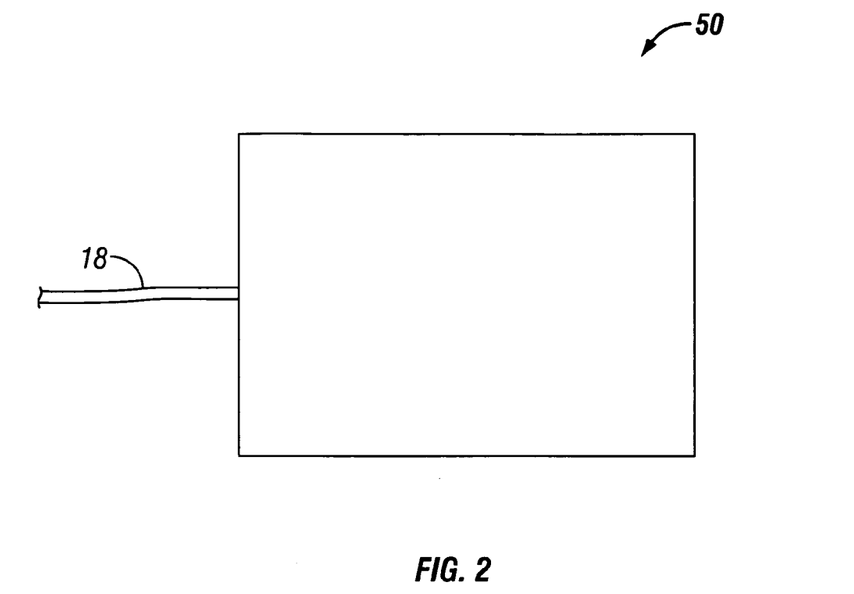
FIG. 2 is a top plan view of a temperature regulating return electrode according to an embodiment of the present disclosure.
Figure 3:
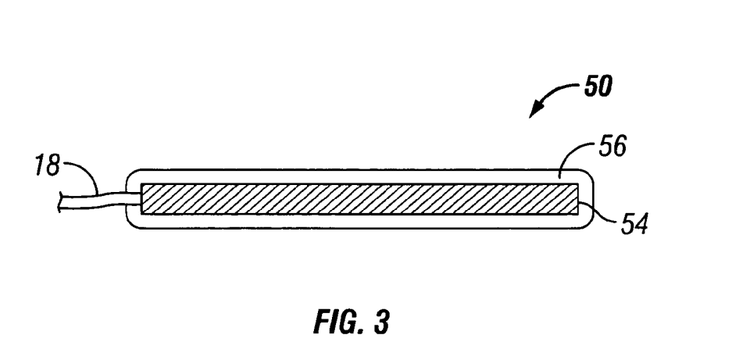
FIGS. 3 and 3a are cross-sectional views of a temperature regulating return electrode according to embodiments of the present disclosure.
Figure 3A:
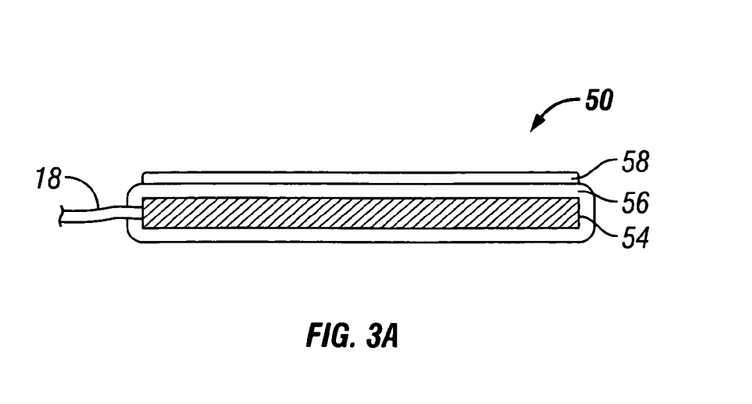

FIGS. 2, 3 and 3a illustrate various embodiments of return electrode 50 for use in monopolar electrosurgery. Generally, the return electrode 50 is a pad having a top surface and a bottom surface configured to receive current during monopolar electrosurgery. While FIG. 2 depicts the return electrode 50 in a general rectangular shape, it is within the scope of the disclosure for the return electrode 50 to have any regular or irregular shape. Although electrosurgical references to "monopolar electrosurgery" and "bipolar electrosurgery" are made in the context of the application, one should appreciate that these references are simply exemplary embodiments of the present disclosure and form no limitation on the present disclosure. In fact, the present disclosure may extend to and encompass any surgery or diagnostic practices using radiofrequency energy.

Generally, the area of the return electrode 50 that is in contact with the patient 20 affects the current density of the signal that heats the tissue. The smaller the contact area the return electrode 50 has with the patient 20, the greater the current density and the greater and more concentrated the heating of tissue. Conversely, the greater the contact area of the return electrode 50, the smaller the current density and the less heating of the tissue. Further, the greater the heating of the tissue, the greater the probability of possibly burning the tissue. Although many other safeguards may be present in the electrosurgical generator to prevent and minimize such risks, it is important to either ensure a relative high amount of contact area between the return electrode 50 and the patient 20, or otherwise maintain a relatively low current density on the return electrode 50.

While there are various methods of maintaining a relatively low current density (including, inter alia, the use of electrosurgical return electrode monitors (REMs), such as the one described in commonly-owned U.S. Pat. No. 6,565,559, the contents of which are hereby incorporated by reference herein in its entirety), the present disclosure ensures the return electrode 50 maintains a low current density by distributing the temperature created by the current over the surface of the return electrode 50.

Current density at the return electrode 50 is reduced via a positive temperature coefficient (PTC) material 56 disposed on the return electrode 50. As best illustrated in FIG. 3, return electrode 50 includes a conductive body 54 coated with a PTC material 56. It is also within the scope of this disclosure for the return electrode 50 to be comprised of several layers, one or more of which layer being a PTC material 56. The PTC material 56 can be made of, inter alia, polymer/carbon based material, a cermet based material, a polymer material, a ceramic material, a dielectric material, or any combinations thereof, or still alternatively can be made from a polymer/carbon material. An example of such material that can be used for the PTC material is described in U.S. Pat. No. 6,132,426, the contents of which is herein incorporated by reference in its entirety, and is known as "PolySwitch RTM" made by the Raychem Corporation of California.

The PTC material 56 acts to distribute the temperature created by the current over the surface of the return electrode 50 to minimize the risk of patient burns. The PTC material 56 regulates the temperature over the area of the return electrode 50 by responding to increases in temperature with an increase in resistance in localized areas. The increase in resistance reduces the current in the localized area, thus causing the current to conduct more in the areas with lower resistance or lower temperature. Further, as current is applied through the PTC material 56 of return electrode 50, power is dissipated and the temperature is increased. The increase in temperature increases the resistance and limits the current, thus reducing the heating effect. This results in a return electrode 50 with a temperature that is substantially uniform throughout its entire surface and with varying levels of resistance. Consequently, there are no localized "hot spots," which c an cause patient burns. As the overall temperature increases, consequently increasing the resistance, an REM (return electrode monitoring) circuit can detect and measure such increases and turn off an RF supply when a predetermined temperature has been exceeded.

In one embodiment, an adhesive layer 58 may be disposed on the PTC material 56 of return electrode 50, as illustrated in FIG. 3A. The adhesive layer 58 can be made of, but is not limited to, a polyhesive adhesive, a Z-axis adhesive or a water-insoluble, hydrophilic, pressure-sensitive adhesive. The function of the adhesive layer 58 is to ensure an optimal surface contact area between the return electrode 50 and the patient 20 and thus to further limit the possibility and any risks of a patient burn.

Figure 5:
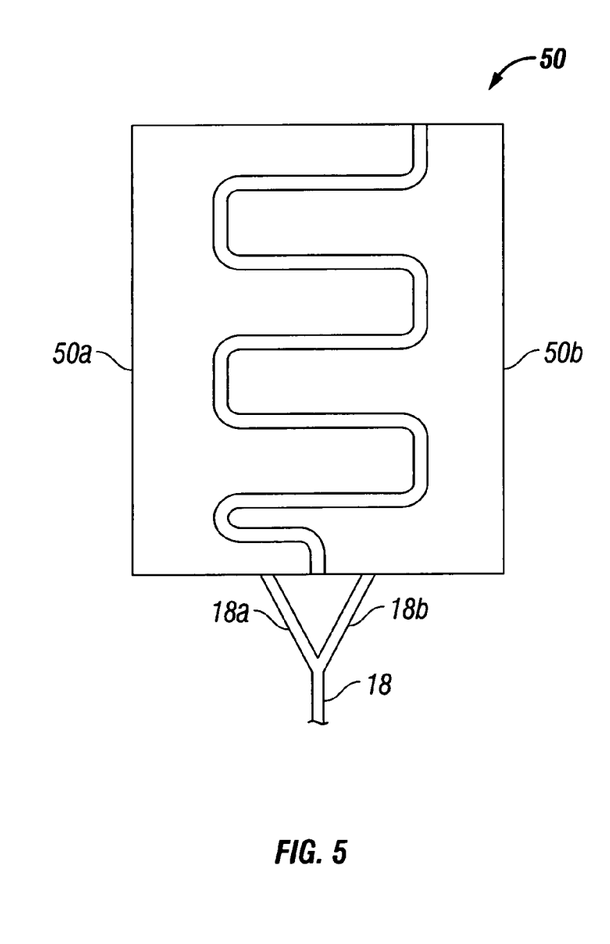
FIG. 5 is a temperature regulating return electrode according to an embodiment of the present disclosure.

Return electrode 50 may be also split into a plurality of parts, depicted as two parts 50a and 50b in FIG. 5. This embodiment enables various measurements (e.g., temperature, current, contact quality, impedance, etc.) to be taken between the return electrodes 50a and 50b. Wires 18a and 18b return energy from each part 50a and 50b, respectively, of return electrode 50 back to generator 14. Wires 18a and 18b can be combined to form a single cable 18 (as illustrated in FIG. 5) or wires 18a and 18b can remain as individual wires (not shown) to return energy from return electrode 50 back to generator 14. A split return electrode 50 may be connected to an REM via multiple REM wires (not shown), each being connected to a part, e.g., 50a or 50b, of return electrode 50.

Figure 4:
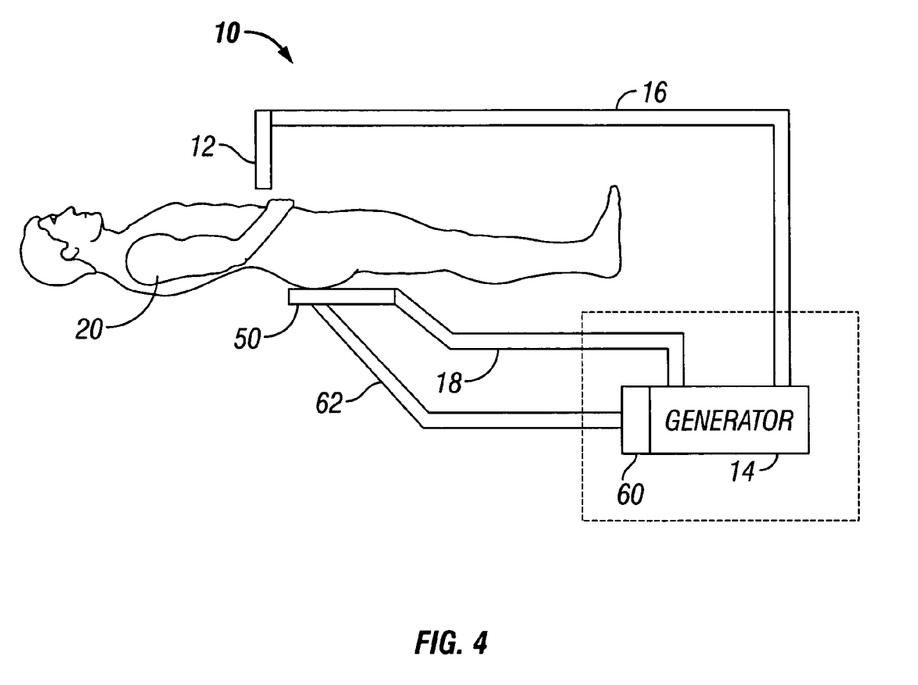
FIG. 4 is a schematic illustration of a monopolar electrosurgical system including a return electrode monitor (REM)

Referring now to FIG. 4, a schematic illustration of a monopolar electrosurgical system including a return electrode monitor (REM) is shown. In addition to regulating the temperature across the surface of the return electrode 50, the return electrode 50 with the PTC material 56 also acts as a thermistor or monitor for the temperature. This may be accomplished by using an REM circuit 60. The REM circuit 60 has a synchronous detector that supplies an interrogation current sine wave of about 140 kHz across both return electrodes 50a and 50b of the return electrode 50 and the patient 20 via wire 62. The REM circuit 60 is isolated from the patient 20 via a transformer(see FIG. 6). The impedance in the return electrode 50 is reflected back from the patient 20 to the REM circuit 60 via wire 18. The relationship between temperature and impedance can be linear or non-linear. By measuring the resistance across the two return electrodes 50a and 50b, the REM circuit 60 is able to monitor the overall temperature at the return electrode 50 and the contact quality of the return electrode 50. The relationship between temperature and resistance can also be linear or non-linear (an illustration of a non-linear relationship is depicted in FIG. 7). In this embodiment, the generator 14 would be disabled when the total increase in resistance or temperature of the return electrode 50 reaches a predetermined value. Alternatively, there may be several threshold values, such that when a first threshold is exceeded, the output power of the generator is reduced and, when a subsequent second threshold value is exceeded, the generator 14 is shutdown. This embodiment can be adapted to provide temperature regulation (achievable utilizing a PTC coating), temperature monitoring, current monitoring and contact quality monitoring for the return electrode 50, thus greatly reducing the probability of a patient burn.

Figure 5A:
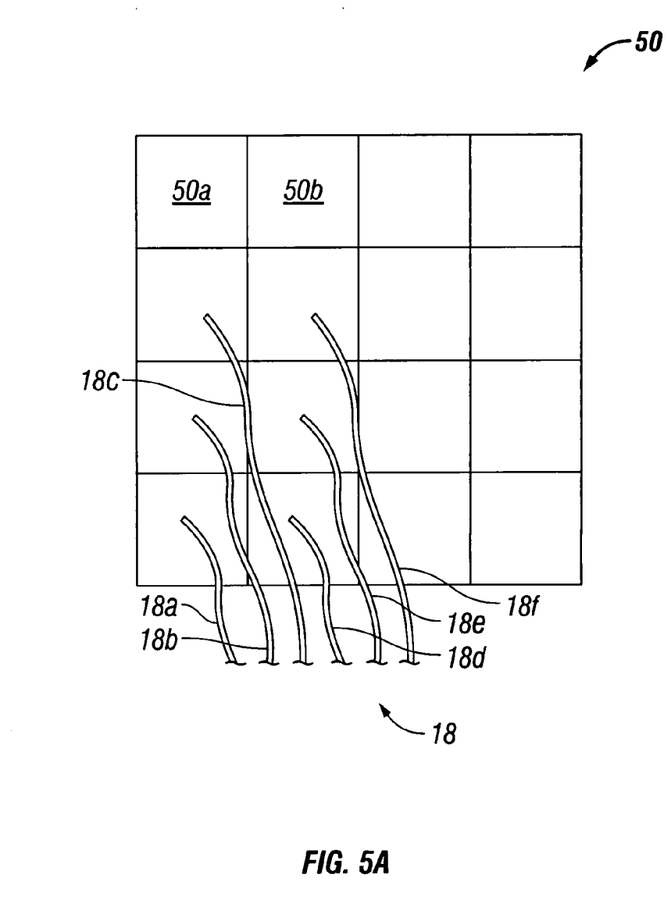
FIG. 5A is a temperature regulating return electrode according to another embodiment of the present disclosure.

In one embodiment, a plurality of wires 18a-18f may be disposed on the return electrode 50, such that the wires are spaced to substantially form a grid or matrix pattern, as illustrated in FIG. 5A. In this embodiment, several measurements can be calculated at various places on the return electrode 50 by determining the resistance between any two wires, e.g., wires 18a and 18b. Each square portion 50a, 50b, etc. of return electrode 50 may have a wire 18 coupled to it, but only wires 18a-18f are shown for clarity. This embodiment can also be adapted to provide temperature regulation, temperature monitoring, current monitoring and contact quality monitoring for the return electrode 50, thus greatly reducing the probability of a patient burn.

Figure 6:
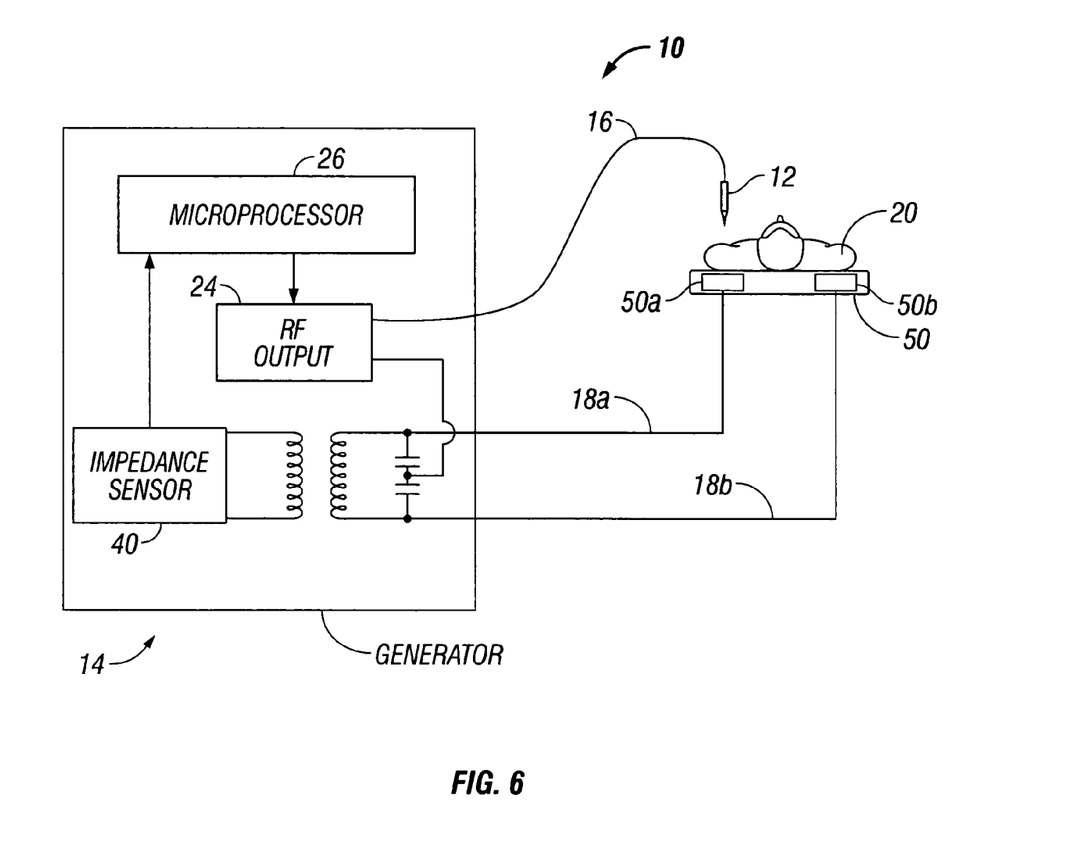
FIG. 6 is a schematic block diagram of a return electrode monitoring system.
Figure 7:
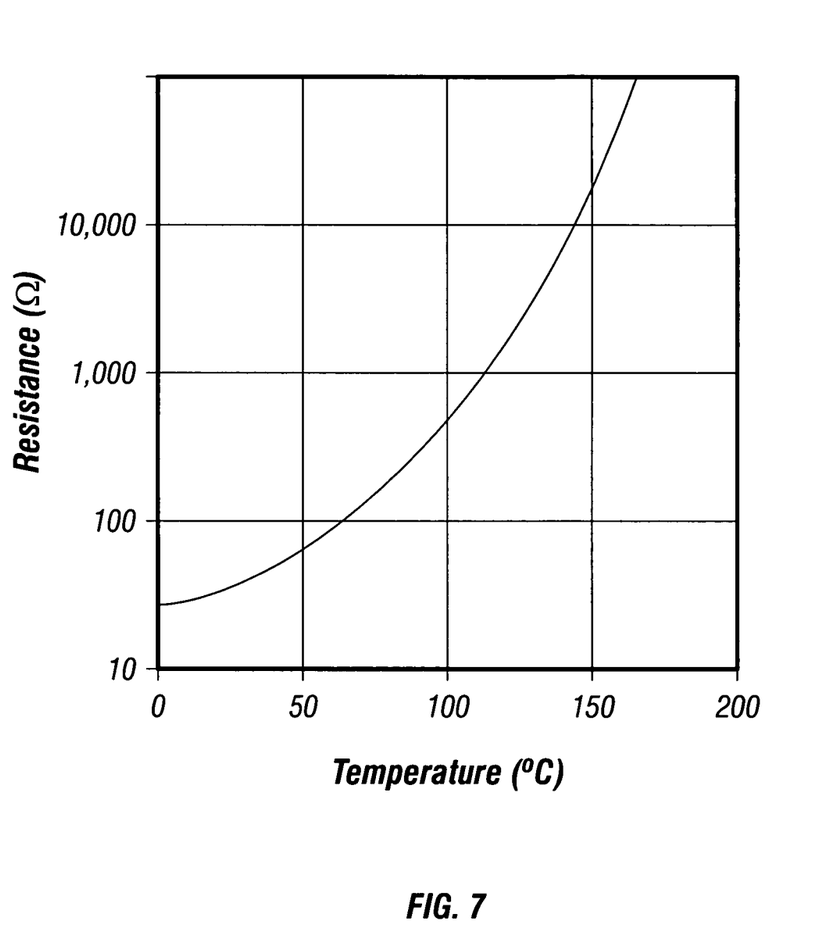
FIG. 7 is an example of a resistance versus temperature graph for a positive temperature coefficient (PTC) material.

Now referring to FIG. 6, a schematic view of an electrosurgical generator 14 incorporating an REM circuit is shown. The electrosurgical generator 14 includes a microprocessor 26, an RF output stage 24 for generating an output voltage and output current for transmission to the surgical instrument 12, and an impedance sensor 40 for measuring the impedance between the split pads 50a and 50b of the return electrode 50 to determine the degree of adherence of the return electrode 50.

The REM circuit measures the total resistance of the return electrode 50. When the overall temperature on either or both return electrodes 50a or 50b is increased, the PTC coating increases the resistance. The REM circuit measures the temperature increase and thus inhibits the output of the generator 14. The REM circuit also measures the resistance and inhibits the output of the generator 14 if the patient impedance increases due to the return electrode 50 becoming partially or completely removed from the patient 20.

Figure 8:
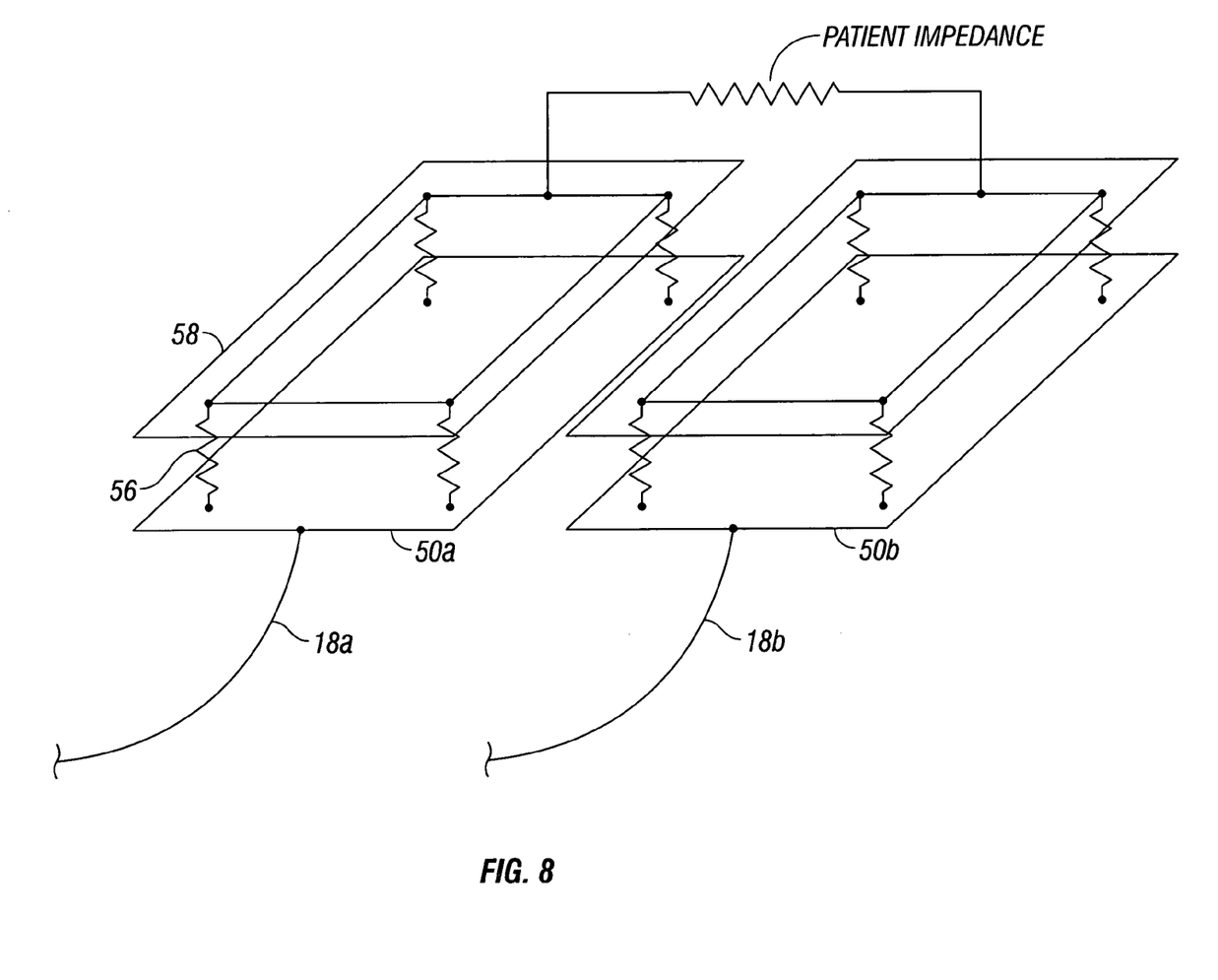
FIG. 8 is a schematic illustration of a return electrode with a PTC material and an adhesive layer according to an embodiment of the present disclosure.

The return electrode 50 with a PTC layer 56 is schematically illustrated in FIG. 8. The PTC layer 56 is shown placed over each of the two return electrodes 50a and 50b. The PTC material 56 is a layer of a continuous coating of parallel resistors, illustrated as four resistors per return electrode 50 for clarity. A conductive adhesive layer 58 is shown above the PTC material 56 and is configured to maintain contact between the return electrode 50 and the patient 20 and for conducting RF energy back to the generator 14. The return electrodes 50a and 50b enable the patient impedance to be measured. The patient impedance is in a series connection with the two return electrodes 50a and 50b and the PTC material 56.

In the embodiment illustrated in FIG. 6 with a split return electrode 50, an impedance sensor 40 may form part of the return electrode circuit. The impedance sensor 40 measures the impedance between the return electrodes 50a and 50b to determine the degree of adherence of the return electrode 50. That is, if a portion of the return electrode 50 becomes detached from the patient 20, the impedance will increase. The impedance sensor 40 transmits a signal indicative of the measured impedance to an input port of the microprocessor 26. An algorithm stored in a memory or in the microprocessor 26 factors in the impedance measurement when determining whether to adjust or terminate a power supply.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

What is claimed is:

1. An electrosurgical return electrode for use in monopolar surgery comprising:
    a conductive pad having a top surface and a bottom surface, wherein a positive temperature coefficient (PTC) material is disposed on the conductive pad such that the PTC material entirely encompasses the conductive pad, the PTC material configured to spread temperature substantially uniformly over the entire top and bottom surfaces by responding to increases in localized temperature with a local increase in resistance.

2. The electrosurgical return electrode of claim 1, wherein the pad includes at least two layers.

3. The electrosurgical return electrode of claim 2, wherein at least one of the at least two layers is the PTC material.

4. The electrosurgical return electrode of claim 1, wherein at least a portion of the top surface of the pad defines a patient contacting surface.

5. The electrosurgical return electrode of claim 4, further comprising an adhesive material disposed on the patient contacting surface.

6. The electrosurgical return electrode of claim 5, wherein the adhesive material is selected from the group consisting of a polyhesive adhesive, a water-insoluble, hydrophilic, pressure-sensitive adhesive, a Z-axis adhesive, and any combinations thereof.

7. The electrosurgical return electrode of claim 1, further comprising a second conductive pad operably coupled to the conductive pad.

8. The electrosurgical return electrode of claim 7, wherein each of the conductive pad and the second conductive pad is coupled to respective wires.

9. The electrosurgical return electrode of claim 1, wherein the PTC material is selected from the group consisting of a polymer/carbon based material, a cermet based material, a polymer material, a ceramic material, a dielectric material, and any combinations thereof.

10. A system for eliminating patient burns during monopolar surgery, comprising:
    a generator configured to generate current;
    an active electrode adapted to couple to the generator and being configured to supply the current to a patient; and
    a return electrode adapted to couple to the generator, the return electrode having a surface configured to receive the current from the patient and return the current to the generator, wherein a positive temperature coefficient (PTC) material is disposed on the return electrode such that the PTC material entirely encompasses the return electrode, the PTC material configured to spread the temperature substantially uniformly over the entire surface of the return electrode.

11. The system for eliminating patient burns of claim 10, further comprising a temperature regulation device disposed in the generator configured to regulate the temperature of at least the return electrode.

12. The system for eliminating patient burns of claim 10, further comprising a temperature monitoring device disposed in the generator configured to monitor the temperature at the return electrode.

13. The system for eliminating patient burns of claim 12, further comprising a generator disabling device configured to disable the generator when the temperature of the return electrode reaches a predetermined value.

14. The system for eliminating patient burns of claim 10, wherein the generator includes a device configured to monitor at least one of the temperature and a contact quality of the return electrode.

15. The system for eliminating patient burns of claim 10, wherein the PTC material is configured to regulate current density at the return electrode.

16. The system for eliminating patient burns of claim 10, further comprising a second conductive pad operably coupled to the conductive pad.

17. The system for eliminating patient burns of claim 16, wherein the conductive pad is coupled to a first wire and the second conductive pad is coupled to a second wire and the system is configured to determine a parameter between the first and second wires.

18. The system for eliminating patient burns of claim 17, wherein the parameter is selected from the group consisting of power, resistance, impedance, and any combination thereof.

19. A method for eliminating patient burns while performing monopolar surgery, the method comprising the steps of:
placing a return electrode with a positive temperature coefficient (PTC) material disposed on and entirely encompassing the return electrode in contact with a patient;
generating electrosurgical energy from an energy source; and
supplying the electrosurgical energy to the patient via an active electrode;
wherein the PTC material on the return electrode spreads the temperature substantially uniformly over the entire surface of the return electrode by responding to increases in localized temperature with a local increase in resistance.

20. An electrosurgical system comprising:
a generator having at least a processor disposed therein, the electrosurgical generator being configured to supply electrosurgical energy to tissue;
a supply electrode adapted to connect to the generator configured to supply the electrosurgical energy to the tissue;
a return electrode having a positive temperature coefficient (PTC) material disposed on and entirely encompassing the return electrode, the PTC material configured to spread a temperature of the return electrode substantially uniformly over the entire surface thereof, the return electrode adapted to connect to the generator and configured to return the electrosurgical energy to the generator, said return electrode including an impedance sensor being configured to measure impedance values between a plurality of return electrode portions and output the impedance values to the at least one processor for determination of a contact reading, the processor operable to compare the contact reading to a stored threshold reading to determine a degree of adherence of the return electrode on the patient.

21. The electrosurgical system of claim 20, wherein said processor adjusts radiofrequency energy to the patient when said contact reading reaches a threshold value.

22. The electrosurgical system of claim 20, wherein the PTC layer is a substantially continuous coating of parallel resistors.

23. The electrosurgical system of claim 20, further comprising a conductive adhesive layer in contact with the PTC layer, said adhesive layer configured to maintain contact between the plurality of return electrode portions and the patient.

* * * * *

UNITED STATES PATENT AND TRADEMARK OFFICE
CERTIFICATE OF CORRECTION

| | |
|---|---|
| PATENT NO. | : 8,821,487 B2 |
| APPLICATION NO. | : 11/395683 |
| DATED | : September 2, 2014 |
| INVENTOR(S) | : Arts et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1437 days.

Signed and Sealed this
Twenty-third Day of February, 2016

Michelle K. Lee
*Director of the United States Patent and Trademark Office*